United States Patent [19]

Ishii et al.

[11] Patent Number: 4,985,592
[45] Date of Patent: Jan. 15, 1991

[54] PROCESS FOR THE PREPARATION OF UNSATURATED CARBOXYLIC ACIDS

[75] Inventors: Hiromichi Ishii; Hideo Matsuzawa; Masao Kobayashi; Kazuhiro Ishii, all of Otake, Japan

[73] Assignee: Mitsubishi Rayon Company, Ltd., Tokyo, Japan

[21] Appl. No.: 952,111

[22] Filed: Oct. 17, 1978

Related U.S. Application Data

[63] Continuation of Ser. No. 666,565, Mar. 15, 1976, abandoned.

[30] Foreign Application Priority Data

Mar. 17, 1975 [JP] Japan ............................. 50-31055
Aug. 1, 1975 [JP] Japan ............................. 50-94512

[51] Int. Cl.$^5$ .................... C07C 51/25; C07C 57/055
[52] U.S. Cl. .................................. 562/534; 502/209; 562/536
[58] Field of Search .............. 562/534; 252/435, 437; 502/209

[56] References Cited

U.S. PATENT DOCUMENTS 3,976,688 8/1976 Akiyama et al. .................... 562/534
4,017,423 4/1977 White et al. ........................ 562/534

Primary Examiner—Vivian Garner
Attorney, Agent, or Firm—Oblon, Spivak, McClelland, Maier & Neustadt

[57] ABSTRACT

The gas phase catalytic oxidation of an unsaturated aldehyde with molecular oxygen at 200° to 500° C. to give the corresponding unsaturated carboxylic acid is conducted in the presence of a catalyst represented by the following formula:

$$Mo_{12}P_aX_bY_cZ_dO_e$$

wherein the subscripts represent the atomic ratios of each component and a is 0.5 to 6, b is 0.001 to 6, c is 0.2 to 6, d is 0 to 6, and e is a value determined by the valencies of the elements present in the catalyst; and Mo is molybdenum, P is phosphorus, O is oxygen, X is at least one metal selected from the group consisting of rhodium, cerium and zirconium, Y is at least one alkali metal selected from the group consisting of potassium, rubidium and cesium, and Z is at least one metal selected from the group consisting of iron, cobalt, nickel, zinc, antimony, silicon, bismuth, cadmium, uranium, manganese, copper, vanadium, niobium and tantalum. This catalyst is especially effective for the preparation of methacrylic acid from methacrolein and has a very long life time.

7 Claims, No Drawings

PROCESS FOR THE PREPARATION OF UNSATURATED CARBOXYLIC ACIDS

This is a continuation of application Ser. No. 666,565, filed Mar. 15, 1976, now abandoned.

BACKGROUND OF THE INVENTION

1. Field of the Invention

This invention relates to a process for preparing unsaturated carboxylic acids from unsaturated aldehydes in the presence of a phosphorus-molybdenum-alkali metal type catalyst.

2. Description of the Prior Art

Various catalysts have been known as being suitable for the gas phase catalytic oxidation of unsaturated aldehydes.

These include, for example, processes for preparing acrylic acid from acrolein by using a catalyst consisting of P, Mo and As (Japanese Patent publication No. 19260/1963) or by using a catalyst consisting of Mo, V, W and silicon (Japanese Patent publication No. 12129/1969). Some of these catalysts have been used on a commercial scale.

Many processes have also been suggested for preparing methacrylic acid. These include, for example, Japanese Patent publication No. 6605/1972 (a Mo-Ni-Ti catalyst) and No. 10773/1973 (a catalyst containing Mo and Tl); U.S. Pat. No. 3,686,294 (a P-Mo-As catalyst) and No. 3795703 (a P, Mo and alkali metal type catalyst); and Belgian Patent No. 817100 (a P, Mo and Sb type catalyst). From the viewpoint of industrial suitability, however, these catalysts are quite insufficient regarding selectivity and lifetime. Consequently, there is still a need for improved catalysts for preparation of methacrolein and/or acrolein.

SUMMARY OF THE INVENTION

Accordingly, it is an object of the present invention to provide a novel catalyst having a long lifetime suitable for preparing acrylic acid or methacrylic acid from acrolein or methacrolein.

Briefly, this and other objects of this invention as will hereinafter be made clear have been attained by providing a process for the preparation of acrylic acid or methacrylic acid which comprises catalytically oxidizing acrolein or methacrolein in the gas phase at a temperature of 200° to 500° C. with molecular oxygen in the presence of a catalyst of the following formula:

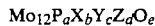

$$Mo_{12}P_aX_bY_cZ_dO_e$$

wherein the subscripts represent the atomic ratio of each component and a is 0.5 to 6, b is 0.001 to 6, c is 0.2 to 6, d is 0 to 6, and e is a value determined by the valencies of the elements present in the catalyst; and wherein Mo is molybdenum, P is phosphorus, O is oxygen, X is at least one metal selected from the group consisting of rhodium, cerium and zirconium, Y is at least one alkali metal selected from the group consisting of potassium, rubidium and cesium and Z is at least one metal selected from the group consisting of iron, cobalt, nickel, zinc, antimony, silicon, bismuth, cadmium, uranium, manganese, copper, vanadium, niobium and tantalum.

DESCRIPTION OF THE PREFERRED EMBODIMENTS

A practical catalyst high in activity, selectivity and lifetime and suitable for use in a process for preparing methacrylic acid from methacrolein has now been discovered. It has been further discovered that this catalyst can be also used in a process for preparing acrylic acid from acrolein.

In the catalyst to be used in the present invention, the chemical states of phosphorus, molybdenum, the alkali metal and the other metals are so complicated that the chemical state of each component element has not been completely elucidated. It seems probable, however, that each component is not simply present in the form of a mere individual oxide but is chemically bonded with the other component oxides.

It is well known that a catalyst system containing phosphorus and molybdenum is effective for the gas phase oxidazation of acrolein or methacrolein. However, phosphorus and molybdenum form very complicated compounds depending on the mixing ratio, heat-treating temperature and atmosphere employed.

In the method of preparing the catalyst of this invention, the catalyst is heat-treated in an atmosphere of air or an inert gas at a temperature of 300° to 600° C. for from 1 hour to scores of hours. The heat-treating atmosphere influences the resultant catalyst activities. An atmosphere of an inert gas such as nitrogen, ammonia, carbon dioxide, carbon monoxide, a hydrocarbon, helium, argon and the like produces a catalyst high in activity.

The reason for the increase in catalyst activity has not been completely elucidated, but it has been determined that when the catalyst of the present invention is heat-treated in an atmosphere of air, the color of the catalyst changes to yellow-green. Moreover, after the catalyst has been used in the process of this invention, the color changes to deep-blue and the phospho-molybdic acid or salt thereof in the catalyst is reduced. On the other hand, when the catalyst is heat-treated in an atmosphere of nitrogen gas, the color changes to dark-green showing that the catalyst has been further reduced. After the catalyst is used in the process, the color returns to a deep-blue which shows that the catalyst is oxidized by the oxygen in the reaction feed gas. From these facts, it is believed that in the catalyst of the present invention, the half-reduced phospho-molybdic acid or salt thereof is quite significant for catalyst activity, and that the half-reduced catalyst which comes from the reduced catalyst described above has a higher activity than does one which comes from the aforementioned oxidized catalyst.

When a catalyst containing phosphorus and molybdenum is used for a gas phase oxidation, the activity and selectivity will often be reduced by variations in the catalyst structure occurring with increased use and reaction time. This tendency increases as the reaction temperature is elevated.

The increase in catalyst activity, therefore, is an important practical consideration because with higher activities the oxidation reaction can be performed at lower temperature and the catalyst lifetime can be prolonged.

Among the metals represented by X in the catalyst of the present invention, rhodium is particularly preferred in respect of the selectivity to methacrylic acid that is displayed.

The atomic ratio of the metal represented by Z must be within the range of 0 to 6, especially 0.01 to 6, when molybdenum is 12. When two or more of these metals are present, it is preferred that the sum of the atomic ratio of the metals is within the above range.

The preparation of the catalyst to be used in this invention can be accomplished according to methods known to those skilled in the art. For example, conventional methods such as evaporation-to dryness, precipitation, oxide-mixing or the like can be used.

The catalyst components may be used on carriers or diluted with such known inert carriers as silica, alumina, silica-alumina and silicon carbide.

Various compounds can be used as starting materials for the catalyst. These include, for example, nitrates, ammonium salts, chlorides, oxides and heteropoly acids such as phosphomolybdic acid.

The reactant unsaturated aldehyde may contain small amounts of impurities which have no influence on the reaction, such as water or a lower saturated aldehyde. The process of this invention is especially effective for the oxidation of methacrolein. Methacrolein which is obtained by the catalytic oxidation of isobutylene or t-butyl alcohol can be used as is or alternatively after being purified.

The concentration of the unsaturated aldehyde in the feed gas can be varied within a broad range, but is preferably 1 to 20% by volume, especially 3 to 15% by volume.

Molecular oxygen is used as the oxidant in the process of this invention. Preferably, air is used from the economic viewpoint. If necessary, an oxidant of air enriched with pure oxygen can also be used. The concentration of oxygen in the feed gas, in terms of the mole ratio relative to the unsaturated aldehyde, should be within the range of 0.3 to 4, especially 0.4 to 2.5. The starting gaseous mixture may be diluted with an inert gas such as nitrogen, steam, carbon dioxide or the like.

The oxidation reaction is conducted under a pressure ranging from atmospheric pressure to several atmospheres. The reaction temperature may be chosen within the range of from 200° to 500° C., preferably 250° to 400° C. The contact time is preably from 0.5 to 10 seconds.

In the process of this invention, both the conversion of methacrolein and the selectivity to methacrylic acid are generally above 80% by moles. This is very significantly higher than the results observed for processes which use catalysts comprising P, Mo and alkali metals or comprising P, Mo, alkali metals and silicon, chromium, aluminum, germanium or titanium.

Having generally described this invention, a further understanding can be obtained by reference to certain specific examples which are provided herein for purposes of illustration only and are not intended to be limiting.

In the following, the parts are by weight. The selectivity to the unsaturated carboxylic acid is the ratio (%) of the molar amount of the desired unsaturated carboxylic acid product to the molar amount of the reacted unsaturated aldehyde.

EXAMPLE 1

42.4 parts of ammonium paramolybdate were dissolved in 85 parts of water. A solution prepared by dissolving 9.75 parts of cesium nitrate in 50 parts of water was added thereto. 0.56 part of solid rhodium chloride was further added and was dissolved. Then, 4.61 parts of 85% phosphoric acid was added. The resulting mixed solution was evaporated to dryness by heating with agitation. The obtained cake was dried at 130° C. for 16 hours, was compression-molded, sieved to a 10 to 20 mesh per inch size and then was calcined at 500° C. under an air current atmosphere for 2 hours to form a catalyst.

The composition of the catalyst was of $P_2Mo_{12}Cs_{2.5}Rh_{0.1}$. This catalyst was packed in a fixed bed vessel and a gaseous mixture of 5% of methacrolein, 10% of oxygen, 30% of steam and 55% of nitrogen (all by volume) was fed into the vessel at a reaction temperature of 325° C. for a contact time of 3.6 seconds. The reaction gas discharged from the vessel was analyzed by gas chromatography. The conversion of the methacrolein was 83.4% and the selectivity to the methacrylic acid was 82.4%. Further, acetic acid, carbon dioxide and carbon monoxide were produced. When the reaction was continued under the same conditions for about 1600 hours, the conversion of the methacrolein was 83.0% and the selectivity to the methacrylic acid was 82.2%.

EXAMPLES 2 AND 3

The following catalysts were prepared in the same manner as in Example 1 except that the atmosphere of the calcination was varied. These catalysts were used for oxidation of methacrolein under the same conditions as in Example 1 except for the reaction temperature.

The results of the experiments are summarized in Table I.

TABLE I

| Example No. | Catalyst Composition (atomic ratio) | atmosphere of calcination of the catalyst | reaction temperature (°C.) | reaction time (hr) | conversion of methacrolein acid role in (%) | selectivity to methacrylic acid (%) |
| --- | --- | --- | --- | --- | --- | --- |
| 2 | $P_2Mo_{12}Cs_{2.5}Rh_{0.1}$ | $N_2$ | 295 | 4 | 82.1 | 83.1 |
| | | | | 1,600 | 82.3 | 83.0 |
| 3 | " | $NH_3$ | 300 | 4 | 82.0 | 82.5 |
| | | | | 1,600 | 82.1 | 83.0 |

EXAMPLES 4 TO 36

The following catalysts were prepared in the same manner as in Example 1 except for the catalyst composition and the atmosphere of calcination which are shown in Table II. These catalysts were used for oxidation of methacrolein under the same conditions as in Example 1 except for the reaction temperature.

The results are shown in Table II.

TABLE II

| Example No. | Catalyst composition (atomic ratio) | atmosphere of calcination of the catalyst | reaction temperature (°C.) | conversion of methacrolein (%) | selectivity to methacrylic acid (%) |
|---|---|---|---|---|---|
| 4 | $P_2Mo_{12}K_{2.5}Rh_{0.1}$ | air | 340 | 78.5 | 78.4 |
| 5 | $P_2Mo_{12}Rb_{2.5}Rh_{0.1}$ | air | 335 | 80.1 | 79.8 |
| 6 | $P_{1.5}Mo_{12}K_2Rh_{0.5}$ | air | 330 | 79.4 | 79.8 |
| 7 | " | $N_2$ | 290 | 80.3 | 80.0 |
| 8 | $P_2Mo_{12}Cs_2Ce_{0.5}$ | air | 320 | 82.4 | 81.8 |
| 9 | " | $N_2$ | 290 | 81.8 | 82.0 |
| 10 | $P_1Mo_{12}Cs_{2.5}Zr_{0.5}$ | air | 325 | 82.5 | 82.5 |
| 11 | " | $N_2$ | 295 | 82.0 | 81.9 |
| 12 | $P_{2.5}Mo_{12}Rb_1Cs_1Rh_{0.3}Ce_{0.2}$ | air | 330 | 83.1 | 82.2 |
| 13 | $P_{2.5}Mo_{12}Rb_1Cs_1Rh_{0.3}Ce_{0.2}$ | $NH_3$ | 295 | 82.8 | 82.5 |
| 14 | $P_2Mo_{12}Cs_2Rh_{0.1}Fe_1$ | air | 310 | 84.1 | 85.6 |
| 15 | $P_2Mo_{12}K_2Rh_{0.1}Fe_1$ | " | 315 | 83.4 | 84.9 |
| 16 | $P_2Mo_{12}Rb_2Rh_{0.1}Fe_1$ | " | 310 | 81.2 | 84.6 |
| 17 | $P_1Mo_{12}K_{2.5}Rh_{0.05}Co_{0.5}$ | " | 305 | 81.3 | 83.2 |
| 18 | $P_2Mo_{12}Cs_2Rh_{0.05}Ni_1$ | " | 315 | 84.8 | 84.5 |
| 19 | $P_2Mo_{12}Cs_2Rh_{0.05}Zn_1$ | " | 320 | 82.7 | 83.3 |
| 20 | $P_1Mo_{12}Cs_1Rh_{0.3}Sb_1$ | " | 315 | 82.9 | 84.7 |
| 21 | $P_1Mo_{12}K_1Cs_1Rh_{0.1}Si_2$ | " | 315 | 83.1 | 84.2 |
| 22 | $P_2Mo_{12}Cs_3Rh_{0.1}Bi_{0.5}$ | " | 315 | 83.5 | 84.2 |
| 23 | $P_2Mo_{12}Cs_3Rh_{0.05}Cd_{0.5}$ | " | 310 | 82.5 | 84.0 |
| 24 | $P_2Mo_{12}Cs_3Rh_{0.03}U_1$ | " | 315 | 83.0 | 84.5 |
| 25 | $P_2Mo_{12}K_2Rh_{0.03}Mn_{0.3}$ | " | 320 | 83.3 | 83.7 |
| 26 | $P_2Mo_{12}K_2Rh_{0.03}Cu_{0.5}$ | " | 320 | 82.9 | 80.0 |
| 27 | $P_{2.5}Mo_{12}Cs_2Rh_{0.03}V_1$ | " | 320 | 84.1 | 82.8 |
| 28 | $P_{1.5}Mo_{12}Cs_1Rh_{0.05}Nb_1$ | " | 315 | 82.4 | 84.6 |
| 29 | $P_{1.5}Mo_{12}Rb_2Rh_{0.05}Ta_1$ | " | 315 | 78.8 | 82.9 |
| 30 | $P_1Mo_{12}K_1Rh_{0.01}Fe_{0.5}Si_{0.5}$ | " | 310 | 81.0 | 85.4 |
| 31 | $P_2Mo_{12}Cs_2Rh_{0.01}Zn_1Sb_1$ | " | 315 | 83.5 | 84.1 |
| 32 | $P_1Mo_{12}Cs_2Rh_{0.01}Bi_{0.3}Cd_{0.7}$ | " | 310 | 79.6 | 82.7 |
| 33 | $P_2Mo_{12}Rb_1Cs_1Rh_{0.01}Mn_{0.5}Ta_2$ | " | 315 | 82.6 | 80.8 |
| 34 | $P_1Mo_{12}K_2Rh_{0.2}Fe_{0.7}Sb_1Bi_{0.3}$ | " | 310 | 84.5 | 85.2 |
| 35 | $P_{1.5}Mo_{12}K_{1.5}Rh_{0.2}Cd_1V_{0.4}U_1$ | " | 310 | 82.2 | 84.0 |
| 36 | $P_2Mo_{12}K_2Rh_{0.03}Co_{0.5}Zn_{0.5}Si_{0.3}Cu_{0.3}$ | " | 310 | 83.1 | 85.8 |

EXAMPLES 37 TO 40

The catalysts of Examples 1, 2, 14 and 19 were used for the oxidation of acrolein. A gaseous mixture of 5% of acrolein, 10% of oxygen, 30% of steam and 55% of nitrogen (all by volume) was fed into the vessel at the temperatures shown in the following Table for a contact time of 3.6 seconds. The reaction gas discharged from the vessel was analyzed by gas chromatography.

The results are shown in Table III.

TABLE III

| Example No. | catalyst composition (atomic ratio) | reaction temperature (°C.) | conversion of acrolein (%) | selectivity to acrylic acid (%) |
|---|---|---|---|---|
| 37 | $P_2Mo_{12}Cs_{2.5}Rh_{0.1}$ | 335 | 90.1 | 91.0 |
| 38 | $P_2Mo_{12}Cs_{2.5}Rh_{0.1}$ | 315 | 91.0 | 90.8 |
| 39 | $P_2Mo_{12}Cs_2Rh_{0.1}Fe_1$ | 310 | 90.5 | 92.6 |
| 40 | $P_2Mo_{12}Cs_2Rh_{0.05}Zn_1$ | 310 | 89.6 | 91.9 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for the preparation of unsaturated carboxylic acids, which comprises catalytically oxidizing acrolein or methacrolein in the gas phase at a temperature of 200° to 500° C. with molecular oxygen to form the corresponding unsaturated carboxylic acids in the presence of a catalyst of the following formula:

$$Mo_{12}P_aX_bY_cZ_dO_e$$

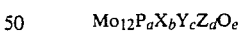

wherein the subscripts represent the atomic ratio of each component and a is 0.5 to 6, b is 0.001 to 6, c is 0.2 to 6, d is 0 to 6, and e is a value determined by the valencies of the elements present in the catalyst; and wherein Mo is molybdenum, P is phosphorus, O is oxygen, X is rhodium, Y is at least one alkali metal selected from the group consisting of potassium, rubidium and cesium, and Z is at least one metal selected from the group consisting of iron, cobalt, nickel, zinc, antimony, silicon, bismuth, cadmium, uranium, manganese, copper, vanadium, niobium and tantalum.

2. The process of claim 1, wherein the atomic ratio of the element Z is 0.01 to 6 when molybdenum is 12.

3. The process of claim 1, wherein the unsaturated aldehyde is methacrolein.

4. A process for the preparation of unsaturated carboxylic acids, which comprises:

catalytically oxidizing acrolein or methacrolein in the gas phase at a temperature of 200° to 500° C. with molecular oxygen to form the corresponding unsaturated carboxylic acid in the presence of a catalyst of the formula:

$$Mo_{12}P_aX_bY_cZ_dO_e$$

wherein the subscripts represent the atomic ratio of each component and a is 0.5 to 6, b is 0.001 to 6, c is 0.2 to 6, d is 0 to 6, and e is a value determined by the valencies of the elements present in the catalyst; and wherein Mo is molybdenum, P is phosphorus, O is oxygen, X is rhodium, Y is at least one alkali metal selected from the group consisting of potassium, rubidium and cesium, and Z is at least one metal selected from the group consisting of iron, cobalt, nickel, zinc, antimony, silicon, bismuth, cadmium, uranium, manganese, copper, vanadium, niobium and tantalum, wherein said catalyst is prepared by forming a mixed oxide catalyst from the oxides, chlorides, nitrates, ammonium salts or heteropoly acids of the elemental constituents of said catalyst, and calcining said mixed oxide catalyst in an inert gas atmosphere at a temperature of 300° to 600° C. for at least one hour.

5. The process of claim 4, wherein said inert gas is nitrogen, ammonia, carbon dioxide, carbon monoxide, a hydrocarbon, helium or argon.

6. The process of claim 5, wherein said inert gas is nitrogen.

7. A process for the preparation of unsaturated carboxylic acids, which comprises catalytically oxidizing acrolein or methacrolein in the gas phase at a temperature of 200° to 500° C. with molecular oxygen to form the corresponding unsaturated carboxylic acids in the presence of a catalyst of the following formula:

$$Mo_{12}P_aX_bY_cO_e$$

wherein the subscripts represent the atomic ratio of each component and a is 0.5 to 6, b is 0.001 to 6, c is 0.2 to 6 and e is a value determined by the valencies of the elements present in the catalyst and wherein Mo is molybdenum, P is phosphorus, O is oxygen, X is rhodium and Y is at least one alkali metal selected from the group consisting of potassium, rubidium and cesium.

* * * * *